(12) United States Patent  
Elia et al.

(10) Patent No.: US 10,864,337 B2  
(45) Date of Patent: Dec. 15, 2020

(54) SYSTEMS AND METHODS FOR TRACKING SPONTANEOUS BREATHING IN A MECHANICALLY VENTILATED PATIENT

(71) Applicant: ART Medical Ltd., Netanya (IL)

(72) Inventors: Liron Elia, Kiryat-Ata (IL); Gavriel J. Iddan, Haifa (IL)

(73) Assignee: ART Medical Ltd., Netanya (IL)

( * ) Notice: Subject to any disclaimer, the term of this patent is extended or adjusted under 35 U.S.C. 154(b) by 0 days.

(21) Appl. No.: 16/000,922

(22) Filed: Jun. 6, 2018

(65) Prior Publication Data

US 2019/0083725 A1 Mar. 21, 2019

Related U.S. Application Data

(60) Provisional application No. 62/560,723, filed on Sep. 20, 2017.

(51) Int. Cl.
*A61M 16/00* (2006.01)
*A61B 5/00* (2006.01)
(Continued)

(52) U.S. Cl.
CPC ......... *A61M 16/024* (2017.08); *A61B 5/037* (2013.01); *A61B 5/113* (2013.01); *A61B 5/1107* (2013.01);
(Continued)

(58) Field of Classification Search
CPC .. A61M 16/024; A61M 16/026; A61M 16/00; A61M 16/0003; A61M 2016/0015;
(Continued)

(56) References Cited

U.S. PATENT DOCUMENTS

| 4,915,103 A * | 4/1990 | Visveshwara | A61M 16/024 128/204.21 |
| 5,065,754 A * | 11/1991 | Jensen | A61M 16/0463 128/200.26 |

(Continued)

FOREIGN PATENT DOCUMENTS

| GB | 2463426 | 3/2010 |
| WO | WO 2016/053574 | 4/2016 |
| WO | WO 2016/112009 | 7/2016 |

OTHER PUBLICATIONS

Lynne Eldridge, MD "What Is a Normal Respiratory Rate?" Medically reviewed by a board-certified physician, Updated Mar. 15, 2019, pertinent information on p. 7.*

(Continued)

*Primary Examiner* — Colin W Stuart

(57) ABSTRACT

There is provided system for monitoring spontaneous breathing of a mechanically ventilated target individual, comprising: a feeding tube for insertion into a distal end of an esophagus of the individual, sensor(s) disposed on the feeding tube at a location such that the sensor(s) is located at the distal end of the esophagus of the individual when the feeding tube is in use, wherein the sensor(s) is positioned for sensing values by contact with the tissue of the esophagus including a lower esophageal sphincter (LES) and/or tissue in proximity to the LES, and code for computing an indication of a frequency band of diaphragm movement of the individual according to an analysis of values sensed by the sensor(s), and for adjustment of parameter(s) of a mechanical ventilator for mechanically ventilating the individual, wherein the instructions for adjustment are computed while the feeding tube is in use.

21 Claims, 12 Drawing Sheets

(51) Int. Cl.
*A61J 15/00* (2006.01)
*A61B 5/03* (2006.01)
*A61B 5/113* (2006.01)
*A61B 5/11* (2006.01)
*A61M 16/04* (2006.01)
*A61M 39/08* (2006.01)

(52) U.S. Cl.
CPC .......... *A61B 5/4836* (2013.01); *A61B 5/7257* (2013.01); *A61J 15/0003* (2013.01); *A61J 15/0084* (2015.05); *A61M 16/0003* (2014.02); *A61M 16/021* (2017.08); *A61M 16/022* (2017.08); *A61M 16/026* (2017.08); *A61B 5/6847* (2013.01); *A61J 15/0049* (2013.01); *A61J 15/0069* (2013.01); *A61M 16/0463* (2013.01); *A61M 2016/0015* (2013.01); *A61M 2016/0018* (2013.01); *A61M 2016/0027* (2013.01); *A61M 2016/0033* (2013.01); *A61M 2039/085* (2013.01); *A61M 2202/0482* (2013.01); *A61M 2205/33* (2013.01); *A61M 2205/3317* (2013.01); *A61M 2205/3331* (2013.01); *A61M 2210/105* (2013.01); *A61M 2210/1014* (2013.01); *A61M 2210/1025* (2013.01); *A61M 2210/1053* (2013.01); *A61M 2230/08* (2013.01); *A61M 2230/40* (2013.01); *A61M 2230/65* (2013.01)

(58) Field of Classification Search
CPC .. A61M 2016/0018; A61M 2016/0021; A61M 16/0051; A61M 2016/0033; A61M 16/003; A61M 16/021; A61M 16/022; A61M 16/0463; A61M 2016/0027; A61M 25/00; A61M 25/10; A61M 2025/0001; A61M 2039/085; A61M 2202/0482; A61M 2230/40; A61M 2230/65; A61M 2205/33; A61M 2205/3303; A61M 2205/3317; A61M 2205/3331; A61M 2210/1014; A61M 2210/1025; A61M 2210/105; A61M 2210/1053; A61J 15/0049; A61J 15/0084; A61J 15/00; A61J 15/0003; A61J 15/0015; A61J 15/0026; A61J 15/003; A61J 15/0046; A61J 15/008; A61B 5/037; A61B 5/7257; A61B 5/6853; A61B 5/113; A61B 5/1107; A61B 5/4836

See application file for complete search history.

(56) References Cited

U.S. PATENT DOCUMENTS

| | | | |
|---|---|---|---|
| 5,520,192 A | 5/1996 | Kitney et al. | |
| 6,584,347 B1 | 6/2003 | Sinderby | |
| 6,588,423 B1* | 7/2003 | Sinderby | ............ A61B 5/04884 128/204.23 |
| 7,472,702 B2 | 1/2009 | Beck et al. | |
| 8,485,980 B2 | 7/2013 | Sinderby et al. | |
| 8,863,742 B2* | 10/2014 | Blomquist | .......... A61M 16/024 128/204.23 |
| 9,585,633 B2* | 3/2017 | Gao | ......................... A61B 8/12 |
| 10,271,739 B2* | 4/2019 | Freeman | ............... A61B 5/0205 |
| 2016/0228661 A1 | 8/2016 | Larsson et al. | |
| 2016/0354063 A1* | 12/2016 | Ward, III | ............. A61B 8/5223 |
| 2018/0078195 A1* | 3/2018 | Sutaria | ................. A61B 5/0402 |

OTHER PUBLICATIONS

Lynne Eldridge, MD "What Is a Normal Respiratory Rate?" Medically reviewed by a board-certified physician, Updated Mar. 15, 2019, pertinent information on p. 7 (Year: 2019).*
International Search Report and the Written Opinion dated Jan. 2, 2019 From the International Searching Authority Re. Application No. PCT/IL2018/050987. (16 Pages).

* cited by examiner

SYSTEMS AND METHODS FOR TRACKING SPONTANEOUS BREATHING IN A MECHANICALLY VENTILATED PATIENT

RELATED APPLICATION

This application claims the benefit of priority under 35 USC § 119(e) of U.S. Provisional Patent Application No. 62/560,723 filed on Sep. 20, 2017, the contents of which are all incorporated by reference as if fully set forth herein in their entirety.

BACKGROUND

The present invention, in some embodiments thereof, relates to treatment of mechanically ventilated patients and, more specifically, but not exclusively, to systems and methods for tracking spontaneous breathing of a mechanically ventilated patient.

Adjustment of ventilation to specific patient needs is a key element in patient survival and recovery. Prolonged mechanical ventilation is associated with significant morbidity and mortality. Patients should be weaned off mechanical ventilation as soon as possible. It is estimated that 40% of the duration of mechanical ventilation is dedicated to the process of weaning.

SUMMARY

According to a first aspect, a system for monitoring spontaneous breathing of a mechanically ventilated target individual comprises: a feeding tube for insertion into a distal end of an esophagus of the mechanically ventilated target individual, at least one sensor disposed near the distal end of the feeding tube at a location such that the at least one sensor is located at the distal end of the esophagus of the target individual when the feeding tube is located within the esophagus and in use, wherein the at least one sensor is positioned for sensing values by contact with the tissue of the esophagus including at least one of a lower esophageal sphincter (LES) and tissue in proximity to the LES, and a non-transitory memory having stored thereon a code for execution by at least one hardware processor of a computing device, the code comprising code for computing an indication of a frequency band of diaphragm movement of the mechanically ventilated target individual according to an analysis of values sensed by the at least one sensor, and computing instructions for adjustment of at least one parameter of a mechanical ventilator for mechanically ventilating the target individual, wherein the instructions for adjustment of at least one parameter of the mechanical ventilator are computed while the feeding tube is in use.

According to a second aspect, a method for monitoring spontaneous breathing of a mechanically ventilated target individual, comprises: providing a feeding tube for insertion into a distal end of an esophagus of the mechanically ventilated target individual, the feeding tube including at least one sensor disposed near a distal portion thereof, sensing values by the at least one sensor, when the at least one sensor is located at the distal end of the esophagus of the target individual when the feeding tube is located within the esophagus and in use, wherein the at least one sensor senses values when contacting the tissue of the esophagus including at least one of a lower esophageal sphincter (LES) and tissue in proximity to the LES, computing an indication of a frequency band of diaphragm movement of the mechanically ventilated target individual according to an analysis of the values sensed by the at least one sensor, and computing instructions for adjustment of at least one parameter of a mechanical ventilator for mechanically ventilating the target individual, wherein the instructions for adjustment of at least one parameter of the mechanical ventilator are computed while the feeding tube is in use.

At least some implementations of the systems, methods, apparatus, and/or code instructions described herein improve the technology of treating mechanically ventilated patients, by improving the process of weaning the mechanically ventilated patient off the ventilator.

At least some implementations of the systems, methods, apparatus, and/or code instructions described herein relate to the technical problem of weaning a patient from a mechanical ventilator. The measurement of frequency of the movement of the diaphragm is indicative of natural breathing tendencies of the ventilated patient, and may be used for synchronization (i.e., synchronization of frequency and phase e.g., a phase-locked loop (PLL)) of the ventilation rate administered by the mechanical ventilator for weaning the patient off the ventilator. When the diaphragm is detected as starting to move to increase the thoracic volume for inhalation of air, the ventilation machine may be set to deliver air. When the diaphragm moves to reduce the volume of the lungs to push out air, the ventilation machine may be set to withdraw air from the lungs of the patient.

A least some implementations of the systems, methods, apparatus, and/or code instructions described herein sense the natural tendency of the intubated patient to breathe without the ventilator. A signal indicating the natural tendency of the intubated patient to breathe without the ventilator may be otherwise difficult to detect, for example, since the natural movement of the diaphragm of the patient is overpowered by the ventilator that forces air in and out of the patient at the frequency set by the ventilator. Signals that include the natural movement of the diaphragm may be drowned by much larger amplitude signals generated based on the ventilator.

At least some implementations of the systems, methods, apparatus, and/or code instructions described herein provide advantages over previously described systems and methods that adjust a ventilator, including:

* At least some implementations of the systems, methods, apparatus, and/or code instructions described herein are designed to adjust a conventional mechanical ventilator that ventilates the patient at a frequency within a normal respiratory rate, for example, about 25-40 breaths per minute, about 20-30 breaths per minus, about 12-18 breaths per minute, about 10-30 breaths per minute, or other values. The rate of the mechanical ventilator is adjusted according to the frequency of the moving diaphragm optionally in an attempt to match the phase of the moving diaphragm, computed as described herein. In contrast, other systems and/or methods may be designed to adjust a high frequency ventilator, which operates at very high ventilation rates that are much higher than normal respiration, for example, 4 times greater than normal.

* At least some implementations of the systems, methods, apparatus, and/or code instructions described herein obtain an accurate indication of the actual motion of the diaphragm based on the analysis of the output of the sensors located at and/or in proximity to the LES (as described herein). In contrast, some other systems and/or methods use neural electrical activity as sensed in the esophagus in the general area of the LES to synchronize the ventilator to the diaphragm, in other words at least some implementations of the system and/or method described herein are designed so that the ventilator tracks as close as possible the natural breathing biomechanical motion of the diaphragm. The neural electrical activity is not indicative of the actual motion of the diaphragm, but represents a demand to inspire from the patient's brain, and not the actual motion of the diaphragm.

* At least some implementations of the systems, methods, apparatus, and/or code instructions described herein obtain an accurate indication of the actual motion of the diaphragm based on filtering out neural signals, since the neural signals form a common mode to the electrode pair. Therefore, the obtained signal indicative of the frequency of movement of the diaphragm, which may have a high millivolt level, has a high signal to noise ratio, from which an accurate value of the frequency of the motion of the diaphragm may be obtained.

A least some implementations of the systems, methods, apparatus, and/or code instructions described herein improve the performance of existing feeding tubes which are positioned with the esophagus of the patient for delivering enteral feedings to the stomach and/or digestive system of the patient. In some implementations, an inflatable esophageal body (e.g., balloon), and/or electrode(s) which may be used for other purposes, for example, to prevent refluxing gastric contents from ascending along the esophagus may be used to measure esophageal wall pressure changes and/or measure impedance value changes which may be analyzed to compute the frequency of patient breathing.

In a further implementation form of the first and second aspects, the at least one sensor comprises an at least one electrode for sensing impedance values.

In a further implementation form of the first and second aspects, the at least one electrode is mounted on an inflatable balloon located at the distal end of the feeding tube, wherein when the inflatable balloon is inflated the at least one electrode contacts the tissue of the esophagus.

In a further implementation form of the first and second aspects, the system further comprises code instructions for and/or the method further comprises at least one esophageal body having a pressure dependent volume, coupled to a distal portion of the feeding tube, wherein the at least one esophageal body contacts the tissue of the esophagus when inflated, and wherein the at least one sensor comprises a pressure sensor that senses the pressure in the at least one esophageal body when inflated.

In a further implementation form of the first and second aspects, the at least one sensor contracting at least one of the LES and tissue in proximity to the LES comprises a pressure sensor that senses pressure changes created by the movement of the diaphragm.

In a further implementation form of the first and second aspects, the at least one parameter comprises a frequency of ventilation cycles.

In a further implementation form of the first and second aspects, the at least one parameter of the mechanical ventilator synchronizes administration of ventilation cycles according to the computed frequency of diaphragm movement.

In a further implementation form of the first and second aspects, the system further comprises code instructions for and/or the method further comprises computing a Fourier transform of a current signal indicative of current values sensed by the at least one sensor, identifying a maximum value of the Fourier transform, and computing the frequency of diaphragm movement according to the frequency and amplitude corresponding to the maximum value.

In a further implementation form of the first and second aspects, the maximum value of the Fourier transform is identified within the range of about 0.2 to 0.5 hertz (Hz).

In a further implementation form of the first and second aspects, the system further comprises code instructions for and/or the method further comprises computing a band pass filter based on values sensed by the at least one sensor during a historical time interval, the band pass filter computed according to a frequency corresponding to a maximum value computed from a Fourier transform of the pressure values obtained during a historical time interval, and according to a frequency bandwidth based on the maximum value, and code for applying the filter to the current signal indicative of pressure values for computing the frequency band of diaphragm movement.

In a further implementation form of the first and second aspects, the frequency bandwidth is computed according to a frequency range in which values of the Fourier transform are at least half of the maximum value.

In a further implementation form of the first and second aspects, the band pass filter comprises a cascade of a low pass filter followed by a high pass filter.

In a further implementation form of the first and second aspects, the system further comprises code instructions for and/or the method further comprises computing a band reject filter according to a spectrum band of the mechanical ventilator, and wherein analyzing comprises removing interference signals of the mechanical ventilator from the values sensed by the at least one sensor by applying the band reject filter to the values sensed by the at least one sensor.

In a further implementation form of the first and second aspects, the at least one sensor is located within about 0-5 centimeters from the lower esophageal sphincter when contacting the tissue of the esophagus.

In a further implementation form of the first and second aspects, the system further comprises code instructions for and/or the method further comprises computing a trend curve according to a plurality of diaphragm movement frequencies measured over a plurality of time intervals, and code for predicting a future frequency of diaphragm movement at a future time interval according to the trend curve.

In a further implementation form of the first and second aspects, the system further comprises code instructions for and/or the method further comprises generating an alert for presentation on a display of a client terminal when the future frequency of diaphragm movement at the future time interval is predicted to meet a requirement.

In a further implementation form of the first and second aspects, the mechanical ventilator is a conventional mechanical ventilator that ventilates the target individual at a frequency within a normal respiratory rate.

In a further implementation form of the first and second aspects, the system further comprises code instructions for and/or the method further comprises computing a filter for filtering of neural signals, and for applying the filter to values sensed by the at least one sensor.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1A:
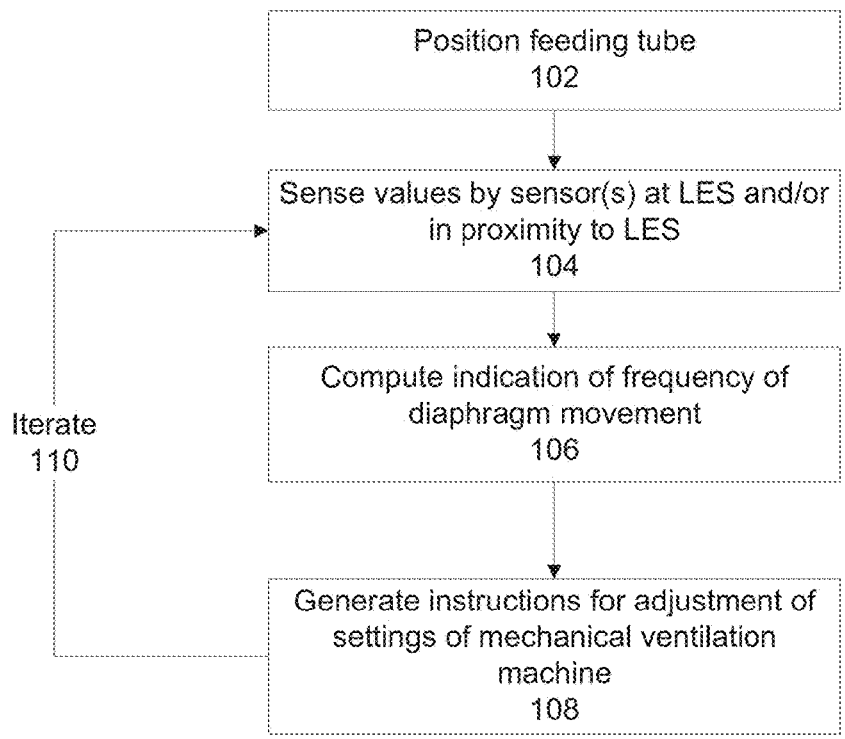
FIG. 1A is a flowchart of a method for monitoring a frequency of diaphragm movement of a mechanically ventilated target individual based on values sensed at the LES and/or in proximity to the LES and adjusting parameter(s) of a mechanical ventilator based on the monitored frequency, in accordance with some embodiments of the present invention.

The present invention, in some embodiments thereof, relates to treatment of mechanically ventilated patients and, more specifically, but not exclusively, to systems and methods for tracking spontaneous breathing of a mechanically ventilated patient.

As used herein, the term frequency may refer to frequency band.

An aspect of some embodiments of the present invention relate to a system, an apparatus, and/or method for monitoring spontaneous breathing of a mechanically ventilated target individual and adjusting parameter(s) of a mechanical ventilator based on the monitored spontaneous breathing signal as sensed by a sensor(s) located within the esophagus. An indication of a frequency band of diaphragm movement waveform of the mechanically ventilated target individual is computed according to an analysis of output of at least one sensor that senses values at the lower esophageal sphincter (LES) and/or of tissues of the esophagus in proximity to the LES. The frequency band is computed since the motion of the diaphragm is not necessarily a pure single harmonic but rather a more general waveform that includes additional frequencies. At least one sensor is located on a distal portion of a feeding tube inserted at least into the distal end portion of the esophagus of the target individual. The computed waveform of diaphragm movement provides an indication of the natural tendency to breath unaided by the target individual. One or more parameters of the mechanical ventilator are adjusted according to the frequency of diaphragm movement for weaning the target individual off the ventilator. The adjustment of the parameter(s) of the mechanical ventilator are adjusted while the feeding tube is in use for enterally feeding the ventilated patient.

Optionally, the at least one sensor includes one or more impedance sensors, optionally electrodes, that sense impedance values. It is noted that impedance may be computed base on voltage value measured by one or more electrodes when one or more currents, optionally alternating currents, are applied. Impedance values measured over a time interval are analyzed to compute the indication of the frequency of movement of the diaphragm.

Alternatively or additionally, the at least one sensor includes a pressure sensor that senses pressure values in an esophageal body (e.g., balloon) inflated within the distal end portion of the esophagus, at the LES and/or in proximity to the LES. Pressure values measured over a time interval are analyzed to compute the indication of the frequency band of movement of the diaphragm.

At least some implementations of the systems, methods, apparatus, and/or code instructions described herein improve the technology of treating mechanically ventilated patients, by improving the process of weaning the mechanically ventilated patient off the ventilator.

At least some implementations of the systems, methods, apparatus, and/or code instructions described herein relate to the technical problem of weaning a patient from a mechanical ventilator. The measurement of frequency of the movement of the diaphragm is indicative of natural breathing tendencies of the ventilated patient, and may be used for synchronization (i.e., synchronization of frequency and phase e.g., a phase-locked loop (PLL)) of the ventilation rate administered by the mechanical ventilator for weaning the patient off the ventilator. When the diaphragm is detected as starting to move to increase the thoracic volume for inhalation of air, the ventilation machine may be set to deliver air. When the diaphragm moves to reduce the volume of the lungs to push out air, the ventilation machine may be set to withdraw air from the lungs of the patient.

A least some implementations of the systems, methods, apparatus, and/or code instructions described herein sense the natural tendency of the intubated patient to breathe without the ventilator. A signal indicating the natural tendency of the intubated patient to breathe without the ventilator may be otherwise difficult to detect, for example, since the natural movement of the diaphragm of the patient is overpowered by the ventilator that forces air in and out of the patient at the frequency set by the ventilator. Signals that include the natural movement of the diaphragm may be drowned by much larger amplitude signals generated based on the ventilator.

At least some implementations of the systems, methods, apparatus, and/or code instructions described herein provide advantages over previously described systems and methods that adjust a ventilator, including:

* At least some implementations of the systems, methods, apparatus, and/or code instructions described herein are designed to adjust a conventional mechanical ventilator that ventilates the patient at a frequency within a normal respiratory rate, for example, about 25-40 breaths per minute, about 20-30 breaths per minus, about 12-18 breaths per minute, about 10-30 breaths per minute, or other values. The rate of the mechanical ventilator is adjusted according to the frequency of the moving diaphragm optionally in an attempt to match the phase of the moving diaphragm, computed as described herein. In contrast, other systems and/or methods may be designed to adjust a high frequency ventilator, which operates at very high ventilation rates that are much higher than normal respiration, for example, 4 times greater than normal.

* At least some implementations of the systems, methods, apparatus, and/or code instructions described herein obtain an accurate indication of the actual motion of the diaphragm based on the analysis of the output of the sensors located at and/or in proximity to the LES (as described herein). In contrast, some other systems and/or methods use neural electrical activity as sensed in the esophagus in the general area of the LES to synchronize the ventilator to the diaphragm, in other words at least some implementations of the system and/or method described herein are designed so that the ventilator tracks as close as possible the natural breathing biomechanical motion of the diaphragm. The neural electrical activity is not indicative of the actual motion of the diaphragm, but represents a demand to inspire from the patient's brain, and not the actual motion of the diaphragm.

* At least some implementations of the systems, methods, apparatus, and/or code instructions described herein obtain an accurate indication of the actual motion of the diaphragm based on filtering out neural signals, since the neural signals form a common mode to the electrode pair. Therefore, the obtained signal indicative of the frequency of movement of the diaphragm, which may have a high millivolt level, has a high signal to noise ratio, from which an accurate value of the frequency of the motion of the diaphragm may be obtained.

A least some implementations of the systems, methods, apparatus, and/or code instructions described herein improve the performance of existing feeding tubes which are positioned with the esophagus of the patient for delivering enteral feedings to the stomach and/or digestive system of the patient. In some implementations, an inflatable esophageal body (e.g., balloon), and/or electrode(s) which may be used for other purposes, for example, to prevent refluxing gastric contents from ascending along the esophagus may be used to measure esophageal wall pressure changes and/or measure impedance value changes which may be analyzed to compute the frequency of patient breathing.

A least some implementations of the systems, methods, apparatus, and/or code instructions described herein do not simply perform automation of a manual procedure, but perform additional automated features which cannot be performed manually by a human using pencil and/or paper. According to current practice, patient weaning is performed based on a spontaneous breathing trial, which is a time consuming manual operation. Moreover, spontaneous breathing trials cannot be performed frequently, which may result in extending patient intubation times longer than necessary. In contrast, some implementations of the systems, methods, apparatus, and/or code instructions described herein gradually adjust the parameters of the ventilator in order to slowly wean the patient off the ventilator guided by the patient's own ability to breathe, rather than a sudden disconnection from the ventilator based on manual practice. Some implementations of the systems, methods, apparatus, and/or code instructions described herein provide automated, real-time, optionally continuous, monitoring of frequency band of diaphragm movement, based on an analysis of values sensed by sensor(s) of a feeding tube which is already in use for feeding the patient. The synchronization of the ventilation machine according to the frequency of diaphragm movement may automate the process of weaning the patient and/or may reduce the time to wean the patient.

When the features related to by the systems, methods, apparatus, and/or code instructions described herein are taken as a whole, the combination of the features amounts to significantly more than a simple mathematical calculation of computing the frequency of diaphragm movement. The systems, methods, apparatus, and/or code instructions described herein do not merely relate to mathematical computations (e.g., equations, Fourier transforms), but relate to the particular data collected, stored, and the way the data is collected by sensors located on the distal end portion of a feeding tube located within the esophagus of the mechanically ventilated target individual that senses values at the LES and/or in proximity to the LES.

A least some implementations of the systems, methods, apparatus, and/or code instructions described herein improve an underlying technical process within the technical field of mechanical ventilation.

A least some implementations of the systems, methods, apparatus, and/or code instructions described herein provide a unique, particular, and advanced technique of weaning a patient off a ventilator.

A least some implementations of the systems, methods, apparatus, and/or code instructions described herein are tied to physical real-life components, for example, one or more of: sensor(s) that sense values at the LES and/or in proximity to the LES, a feeding tube (e.g., nasogastric tube, enteral feeding tube), computational hardware (e.g., hardware processor(s), physical memory device) that analyzes the output of the pressure sensor, a mechanical ventilator, and a display.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1B:
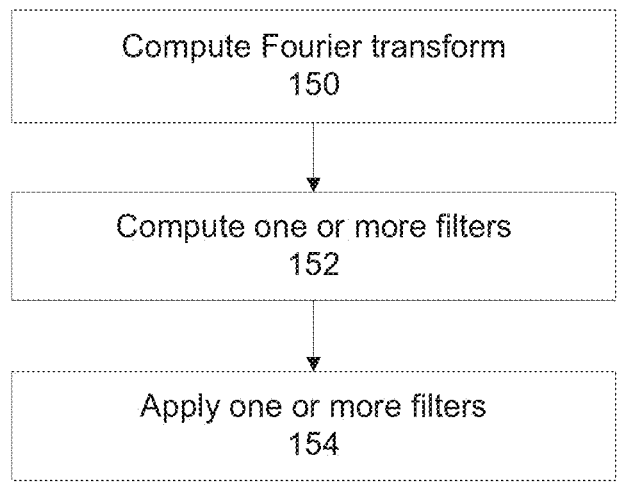
FIG. 1B is a flowchart of an exemplary method for analyzing values sensed at the LES and/or in proximity to the LES by one or more sensors, in accordance with some embodiments of the present invention.
Figure 1C:
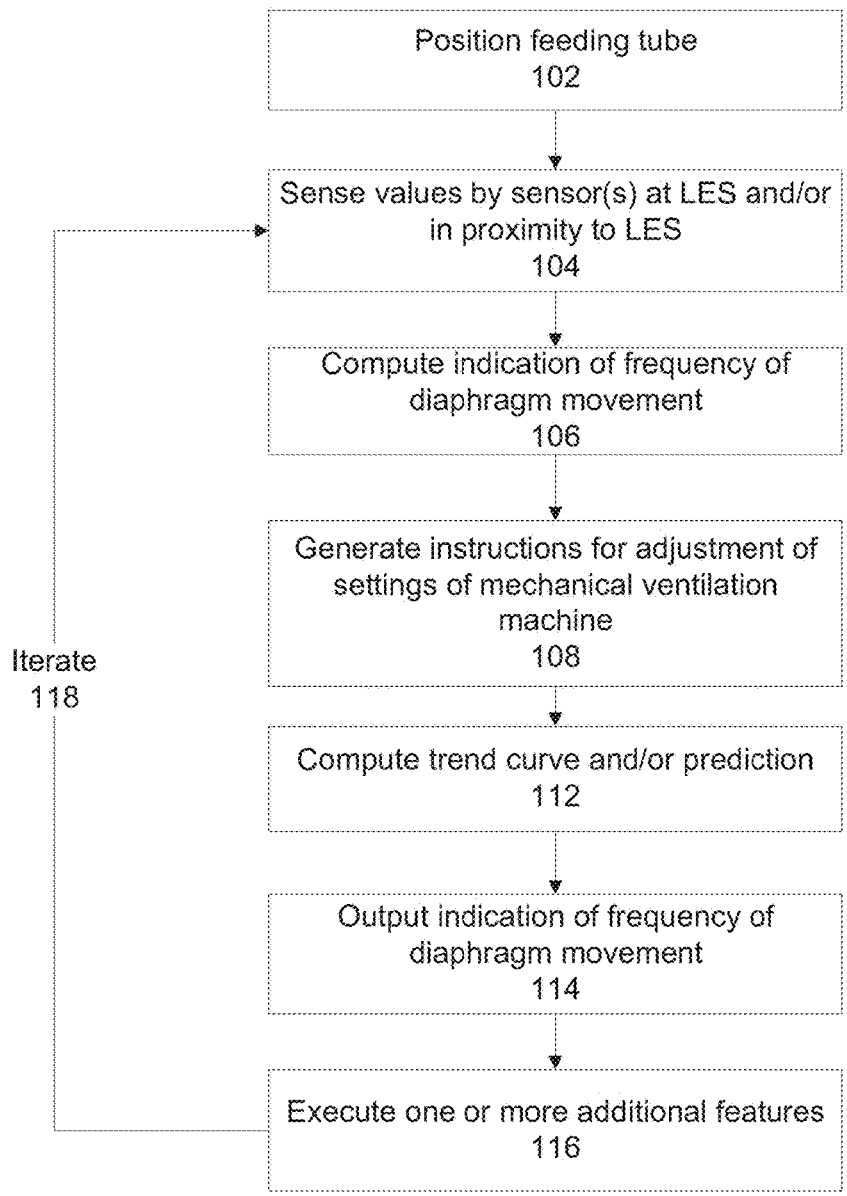
FIG. 1C is the flowchart of the method of FIG. 1A including additional features, in accordance with some embodiments of the present invention.

Reference is now made to FIG. 1A, which is a flowchart of a method for monitoring a frequency of diaphragm movement of a mechanically ventilated target individual based on values sensed at the LES and/or in proximity to the LES and adjusting parameter(s) of a mechanical ventilator based on the monitored frequency, in accordance with some embodiments of the present invention. Reference is also made to FIG. 1B, which is a flowchart of an exemplary method for analyzing values sensed at the LES and/or in proximity to the LES by one or more sensors, in accordance with some embodiments of the present invention. Reference is also made to FIG. 1C, which is the flowchart of the method of FIG. 1A including some additional optional features, in accordance with some embodiments of the present invention.

Figure 2:
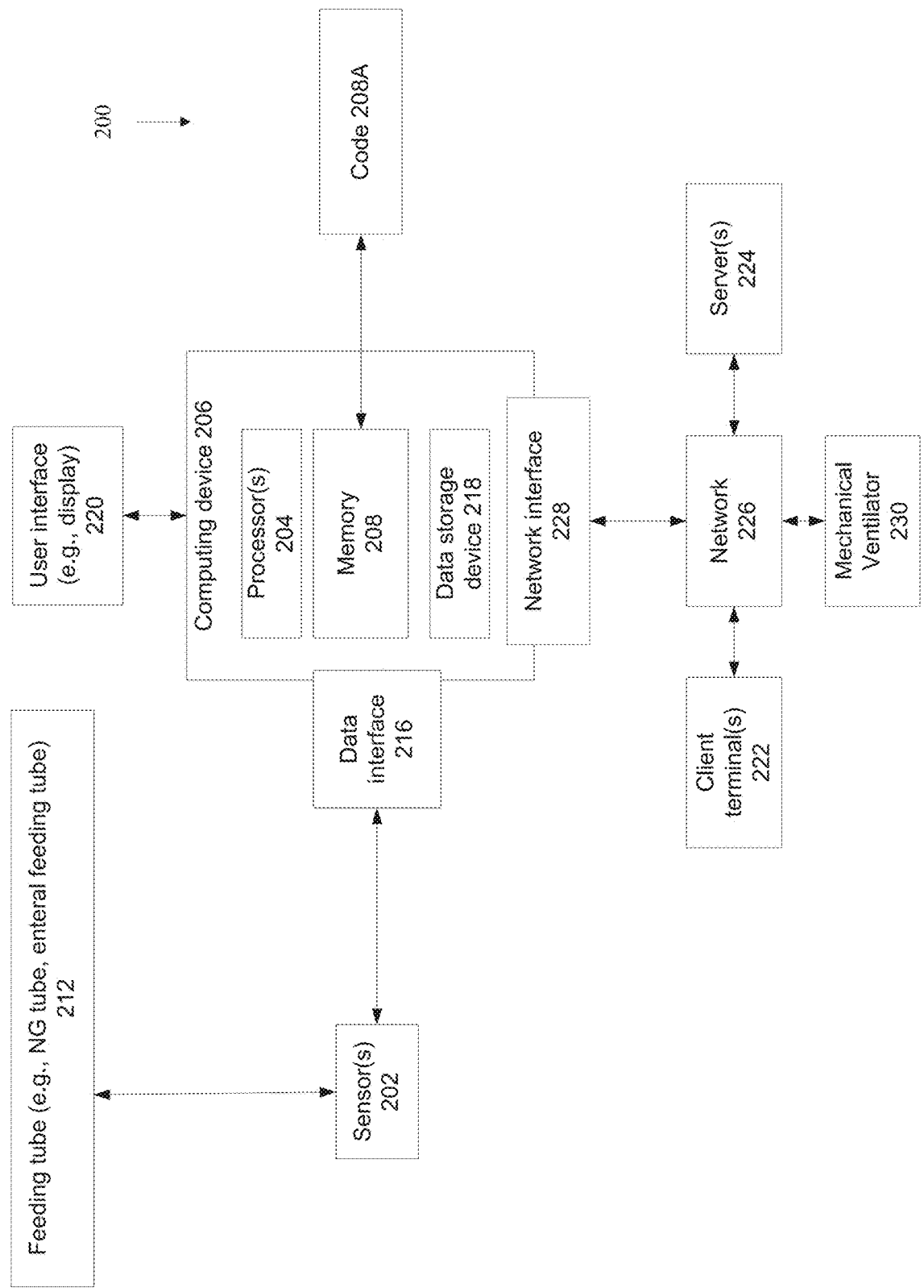
FIG. 2 is a block diagram of a system for monitoring a frequency band of diaphragm movement of a mechanically ventilated target individual based on values sensed at the LES and/or in proximity to the LES and adjusting parameter(s) of a mechanical ventilator based on the monitored frequency, in accordance with some embodiments of the present invention.

Reference is also made to FIG. 2, which is a block diagram of a system 200 for monitoring a frequency band and/or the waveform of diaphragm movement of a mechanically ventilated target individual based on values sensed at the LES and/or in proximity to the LES and adjusting parameter(s) of a mechanical ventilator based on the monitored frequency, in accordance with some embodiments of the present invention. One or more of the acts of the method described with reference to FIGS. 1A-1C may be implemented by components of system 200, as described herein, for example, by a processor(s) 204 of a computing device 206 executing code instructions 208A stored in a memory 208 (also referred to herein as a data storage device).

A feeding tube 212 is implemented as an enteral feeding tube for feeding the patient. The enteral feeding tube is positioned within the gastrointestinal system of the patient, for example, within the stomach, duodenum, or upper small intestine. The frequency of diaphragm movement of mechanically ventilated patients being enterally fed may be monitored without requiring insertion of an additional probe, since the enteral feeding tube is already positioned within the esophagus for feeding the patient. The enteral feeding tube provides an additional function of monitoring the diaphragm movement of the patient i.e., the wave form resulting from the diaphragm movement exerting variable pressure and/or stress on the sensor producing the measured corresponding electrical signal.

Alternatively or additionally, feeding tube 212 is implemented as a nasogastric (NG) tube for evacuation of contents from the stomach. The NG tube is positioned within the gastrointestinal system of the patient, for example, within the stomach, duodenum, or upper small intestine. The said diaphragm movement and resulting signal of mechanically ventilated patients having their stomach contents being drained and/or stomach maintained in a drained state may be monitored without requiring insertion of an additional probe, since the NG tube is already necessary to treat the patient.

Feeding tube 212 includes one or more sensors 202 located at a distal end portion thereof. When feeding tube 212 is in use and positioned within the esophagus for enteral feeding of the patient, sensor(s) 202 is positioned for sensing values within the tissue of the esophagus at the LES and in proximity to the LES (e.g., at the inner wall of the esophagus). Sensor(s) 202 may directly contact the LES and/or tissue of the esophagus, and/or may perform measurements of another element that contacts the LES and/or tissue of the esophagus resulting from the variable pressure generated by diaphragm motion.

Optionally, sensor(s) 202 include impedance sensors, optionally intra-body electrode(s). Impedance sensor(s) are positioned on the distal end of feeding tube 212, such that when feeding tube 212 is inserted into the esophagus of the target patient, Impedance sensor(s) are positioned at the LES and/or in proximity to the lower esophageal sphincter (LES), for example, above the LES within the esophagus, or within the stomach (e.g., the antrum of the stomach).

It is noted that intra-body electrode(s) represents an exemplary implementation of an impedance sensor, and that other implementations of impedance sensors for sensing impedance in proximity to the LES may be used. The terms electrode(s) and impedance sensor(s) may sometimes be interchanged.

Impedance sensor(s) may be implemented, for example, as wires that are exposed on some locations along the feeding tube, where the exposed wires act as impedance sensors, for example, as described with reference to U.S. Pat. No. 9,226,878.

Impedance sensor(s) may located on an inflatable balloon, such that when the balloon is expanded (e.g., inflated) when feeding tube 212 is positioned within the esophagus, contact (optionally by applying a force) is formed between impedance sensor(s) and the inner wall of the esophagus and/or stomach. The contact transmits electrical signals and/or current between intra-body electrode(s) (and/or other implementation of the impedance sensor(s)) and the nearby tissue.

Sensor(s) 202 may be associated with an attachment mechanism, optionally a clip-on attachment, for example, a clip, a C-shaped clip, for connection to existing off-the-shelf feeding tubes 212. Alternatively, enteral feeding tubes are manufactured integrally with sensor(s) 202, for example, sensor(s) 202 are glue, crimped, injection molded, and/or build-in to the outer surface of the enteral feeding tube.

System 200 may include one or more extracorporeal electrode, optionally implemented as a pad electrode. The extracorporeal electrode is designed for placement externally to the skin of the target patient. The extracorporeal electrode may include a sticky portion for sticking to the surface of the skin. The extracorporeal electrode may be positioned over the surface of the skin, with an optional conduction medium (e.g., gel) providing electrical conductivity between the extracorporeal electrode and the skin.

A currently, optionally an alternating current is applied between the intra-body electrode(s) and the extracorporeal electrode(s). Impedance sensor(s) senses the voltage, and the impedance is computed according to the measured voltage.

Alternately, in some implementations, sensor(s) 202 includes one or more esophageal bodies, optionally elastic, located on the distal end of feeding tube 212, for example, an inflatable balloon(s). The esophageal body may be designed to be inflated, for example, in response to identification of an indication of reflux, and/or for sensing lung fluid of the patient. In one example, when inflated, the esophageal body contacts the inner wall of the esophagus, preventing or reducing refluxing digestive (e.g., stomach) contents from ascending via the esophagus. The indication of reflux may be detected, for example, by an analysis of impedance values measured by an electrode(s) located within the esophagus, for example, at the distal end of feeding tube 212. Additional details of an exemplary implementation of feeding tube 212 and esophageal body that is inflated in response to identification of reflux may be found with reference to U.S. Pat. No. 9,226,878, to common inventors and the same assignee. The contents of U.S. Pat. No. 9,226,878 are incorporated herein by reference in their entirety.

Optionally, a pressure sensor senses the pressure in the esophageal body. Pressure sensor at least senses the pressure when the esophageal body is inflated and contacting the inner wall of the esophagus. The pressure sensor may continuously sense the pressure within the esophageal body, for example, for controlling the inflation and/or deflation of the esophageal body.

Alternatively or additionally, miniature pressure and/or stress sensor(s) are mounted on the feeding tube close to the LES impedance sensors for detecting the diaphragm movement as the diaphragm changes the pressure in the LES area.

Optionally, a fluid controller delivers fluid for inflating the esophageal body. The fluid controller may evacuate the fluid out of the esophageal body 214 for deflation of the esophageal body. The fluid controller may be implemented as, for example, one or more pumps, valve(s), fluid syringe(s), and/or combinations of the aforementioned.

Exemplary fluids for inflation of esophageal body include: liquids (e.g., saline, water), and/or gases (e.g., oxygen, nitrogen, carbon dioxide).

Computing device 206 may communicate with sensor(s) 202 via one or more data interfaces 216, for example, a network interface, a wire connection, a wireless connection, a local bus, other physical interface implementations, and/or virtual interfaces (e.g., software interface, application programming interface (API), software development kit (SDK)).

Computing device 206 may be implemented as, for example, a standalone integral unit, a virtual machine, a client terminal, a server, a computing cloud, a mobile device, a desktop computer, a thin client, a Smartphone, a Tablet computer, a laptop computer, a wearable computer, glasses computer, and a watch computer. Computing device 206 may be implemented as a customized unit that include locally stored software and/or hardware that perform one or more of the acts described with reference to FIGS. 1A-1C. Alternatively or additionally, computing device 206 may be implemented as code instructions loaded on an existing computing device. Alternatively or additionally, computing device 206 may be implemented as hardware and/or code instructions (e.g., an accelerator card) installed and/or integrated within an existing computing device.

Processor(s) 204 of computing device 206 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 204 may include one or more processors (homogenous or heterogeneous), which may be arranged for parallel processing, as clusters and/or as one or more multi core processing units. Processor(s) 204 may be hardware processors.

Memory 208 stores code instructions executable by processor(s) 204. Memory 208 is implemented as, for example, a random access memory (RAM), virtual memory, read-only memory (ROM), and/or a storage device, for example, non-volatile memory, magnetic media, semiconductor memory devices, hard drive, removable storage, and optical media (e.g., DVD, CD-ROM). Memory 208 stores code instructions 208A that implement one or more acts of the method described with reference to FIGS. 1A-1C. Alternatively or additionally, one or more acts of the method described with reference to FIGS. 1A-1C are implemented in hardware.

Code instructions 208A may perform one or more features described with reference to act 116 of FIG. 1C, for example: detect a gastric reflux event based on an analysis of impedance value(s) measured by impedance sensor(s) (e.g., electrodes) located on a distal end of the feeding tube optionally at the LES area, and optionally one or more externally located electrodes. When pressure and/or stress sensors are used, the output of the pressure and/or stress sensors is fed to the processor(s). Instructions may be generated for automatically inflating the esophageal body in response to the detected gastric reflux event. Alternatively or additionally, code instructions 208A may sense an amount of lung fluid in the lungs of the target individual based on impedance value(s) measured by impedance sensor(s) (e.g., electrodes) located on a distal end of the feeding tube 212, and optionally one or more externally located electrodes. Instructions may be generated for automatically periodically inflating the esophageal body for periodic sensing of the amount of lung fluid. Computing device 206 may include a data storage device 218 for storing data, for example, a history of diaphragm movement frequencies. Data storage device 218 may be implemented as, for example, a memory, a local hard-drive, a removable storage unit, an optical disk, a virtual memory, a storage device, and/or as a remote server and/or computing cloud (e.g., accessed via a network connection).

Computing device 206 includes and/or is in communication with a user interface 220 that includes a mechanism for a user to enter data (e.g., patient information) and/or view presented data (e.g., computed frequency of diaphragm movement, trend of diaphragm movement frequencies). Exemplary user interfaces 220 include, for example, one or more of, a touchscreen, a gesture device, a display, a keyboard, a mouse, and voice activated software using speakers and microphone. External devices, such as client terminals 222 and/or server(s) 224 communicating with computing device 206 over a network 226 may serve as user interface 220, for example, a smartphone running an application may establish communication (e.g., cellular, network, short range wireless) with computing device 206 over network 226 using a communication interface (e.g., network interface, cellular interface, short range wireless network interface). The user may enter data and/or view data on the display of the smartphone, optionally via a graphical user interface (GUI) application.

Computing device 206 may be in communication with client terminal(s) 222 and/or server(s) 224 over network 226 via a network interface 228. Network interface 228 may be implemented as, for example, a network interface card, a hardware interface card, a wireless interface, a physical interface for connecting to a cable, a virtual interface implemented in software, communication software providing higher layers of connectivity, and/or other implementations.

Client terminal(s) 222 and/or server(s) 224 may receive indications and/or alerts generated by computing device 206, for example, currently computed frequency band of diaphragm movement, computed trend of frequency band of diaphragm movement, warning that the frequency band of diaphragm movement does not meet or requirement or does meet the requirement. Exemplary client terminal(s) 222 include: a mobile device, a smartphone, a tablet computer, a remotely located personal computer, a glasses computer, and a watch computer. Exemplary server(s) 224 include: a hospital medical record server (e.g., the transmitted data may be automatically logged into the patient electronic medical record), and/or a remote monitoring station (e.g., nurses station that monitors multiple patients on the ward).

Computing device 206 may be in communication via network 226 with a mechanical ventilator 230 that mechanically ventilates the target individual. Instructions for adjustment of one or more parameters of mechanical ventilator 230 that are automatically generated by computing device 206 may be transmitted over network 226 to mechanical ventilator 230. After a while the ventilator wave form matches (e.g., as much as possible, and/or within a matching requirement based on a correlation value) the natural diaphragm motion, assisting in the weaning of the patient.

Referring now back to FIG. 1A, at 102, the feeding tube 212 is inserted via the esophagus, into a distal end of an esophagus of a target patient mechanically ventilated by ventilator 230. The feeding tube 212 may be sized and shaped for being disposed within the esophagus so that at least a distal end of the feeding tube 212 is in the stomach lumen of the mechanically ventilated patient, while the segment(s) that include sensor(s) 202 is placed in the esophagus of the patient, optionally the lower portion of the esophagus, for example, above and/or in proximity to the lower esophageal sphincter (LES), for example, at the level of the LES, and/or within about 0-3 centimeters (cm), or about 0-5 cm, or about 0-10 cm of the LES, or other values.

The feeding tube 212 may be an oral tube inserted via the mouth, and/or a nasogastric tube inserted via the nose. The distal end of the feeding tube 212 is designed for positioning within the digestive system when in use for enteral feeding.

The feeding tube 212 is inserted for feeding the mechanically ventilated target individual.

The indication of the frequency of diaphragm movement is computed while the feeding tube is in use for feeding the patient through the impedance sensors and/or the pressure sensors.

Figure 3:
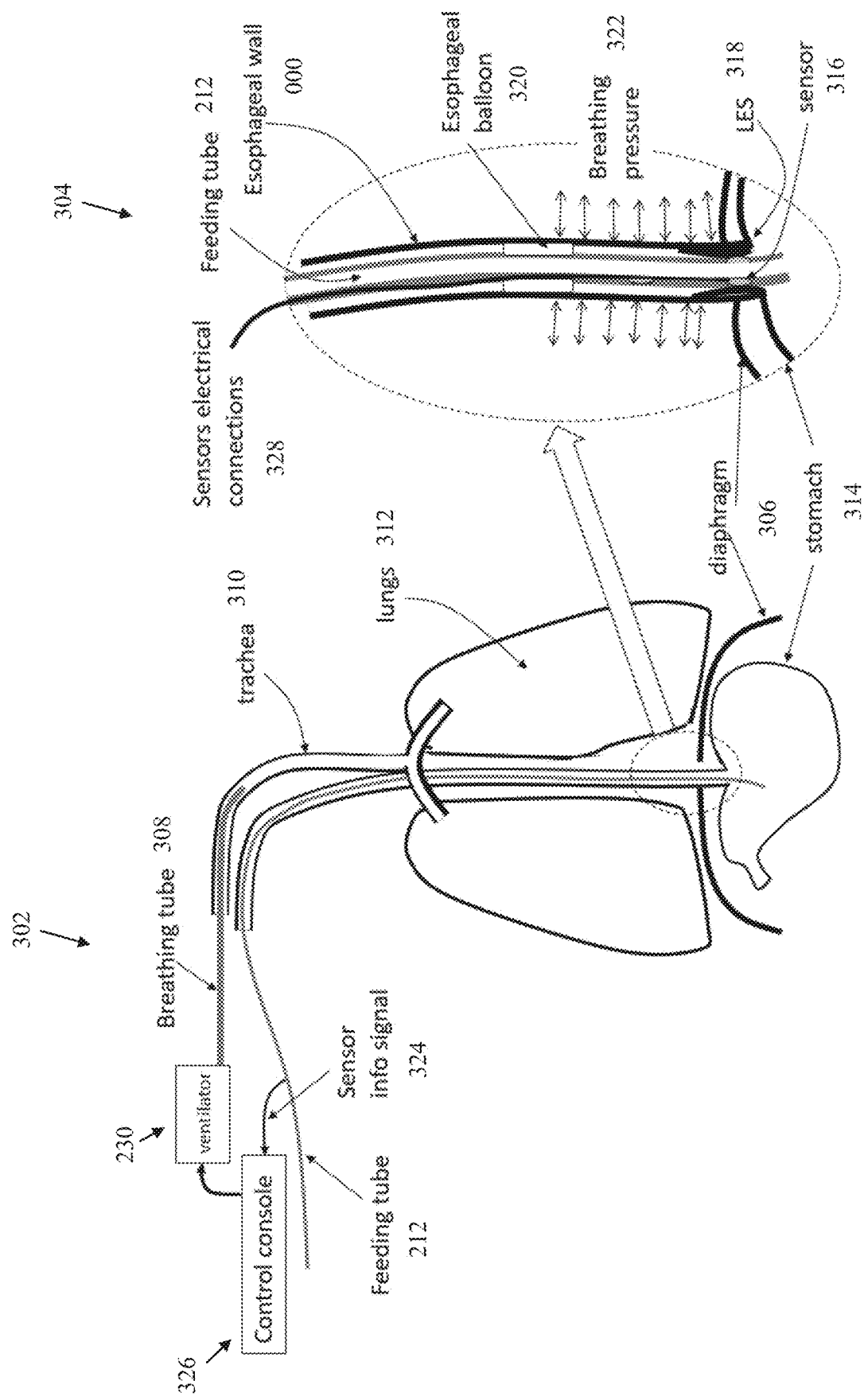
FIG. 3 is a schematic depicting a feeding tube within an esophagus of a target individual mechanically ventilated by a ventilator, and a blow-up of a lower portion of the esophagus illustrating sensing of pressure within the balloon and/or impedance values for computation of frequency of movement of a diaphragm of the target individual, in accordance with some embodiments of the present invention.

Reference is now made to FIG. 3, which is a schematic 302 depicting feeding tube 212 within an esophagus of a target individual mechanically ventilated by ventilator 230, and a blow-up 304 of a lower portion of the esophagus illustrating sensing of balloon pressure and/or impedance values for computation of frequency band of movement of a diaphragm 306 of the target individual, in accordance with some embodiments of the present invention.

A breathing tube 308 located in a trachea 310 of the target individual delivers mechanical ventilation by ventilator 230 to lungs 312 of the target individual. Feeding tube 212 is located within the esophagus of the target individual. The lower portion of feeding tube 212 is positioned within a stomach 314 of the target individual.

Optionally, an impedance sensor 316, optionally implemented as electrode(s) is located on feeding tube 212 at a location in proximity to a lower esophageal sphincter (LES) (and/or the pressure sensors) 318 when feeding tube 212 is in use for feeding the target individual. For example, sensor 316 is located in-line with the LES 318, and/or within about 1-10 centimeters (cm), or about 1-5 cm, or about 1-3 cm below and/or above the LES 318. Alternatively or additionally, an esophageal balloon 320 located on the distal end portion of feeding tube 212, at the location in proximity to the LES 318, is inflated. The breathing pressure 322 within esophageal balloon 320 is sensed by a pressure sensor.

The sensor info signal 324 (i.e., measured impedance values and/or pressure values) are transmitted to a console 326 via sensor electrical connections 328. Console 326 generates instructions for manual and/or automatic adjustment of parameters of ventilator 230 according to the computed frequency band of diaphragm movements computed from the sensor info signal 324.

Referring now back to FIG. 1A, at 104, sensor(s) 202 measure one or more values of the inner wall of the esophagus in proximity to the LES and/or of the LES, for example pressure values within the inflated esophageal body (e.g., balloon), and/or impedance values sensed by electrode(s). Since the sensed values are affected by movement of the diaphragm, an analysis of the sensed values is indicative of the frequency of movement of the diaphragm.

The impedance values may be on the level of millivolt (mV), for example about 1-10 mV, or about 1-100 mV.

When sensor(s) 202 is implemented as impedance sensors (e.g., electrode(s)) that are positioned on a balloon, the electrode(s) may be periodically placed in contact with the inner esophageal wall by inflation of the balloon. Alternatively, the electrode(s) may be in (mostly) constant contact with the tissue of the esophagus in proximity to the LES, for example, when implemented as pairs of wires exposed via an orifice of the feeding tube.

The code further includes instructions for extracting cordial information for better filtering of the desired diaphragm associated signal, for implementation when one or more of the sensors (e.g., impedance and/or pressure) are located near the area where the heart (e.g., apex thereof) effects the esophagus.

In some implementations, sensor(s) 202 sense impedance values with the assistance of one or more externally positioned electrode(s), for example, pad electrodes positioned on the skin of the target individual.

Impedance values may be measured based on an analysis of one or more applied currents, optionally alternating currents, and a measured pressure drop across sensor(s) 202 (e.g., electrode(s)) and/or the externally positioned electrodes.

The values sensed by sensor(s) 202 are recorded over a time interval that may be divided for analysis. Each analyzed time interval is long enough to include multiple ventilator and/or natural breathing cycles, for example, about 1-5 minutes, or 5-10 minutes, or 1-10 minutes, or other values.

The values sensed by sensor(s) 202 may be stored as analogue signals that may be continuous over the time interval, and/or as digital signals that include multiple discrete values over the time interval.

Figure 4:
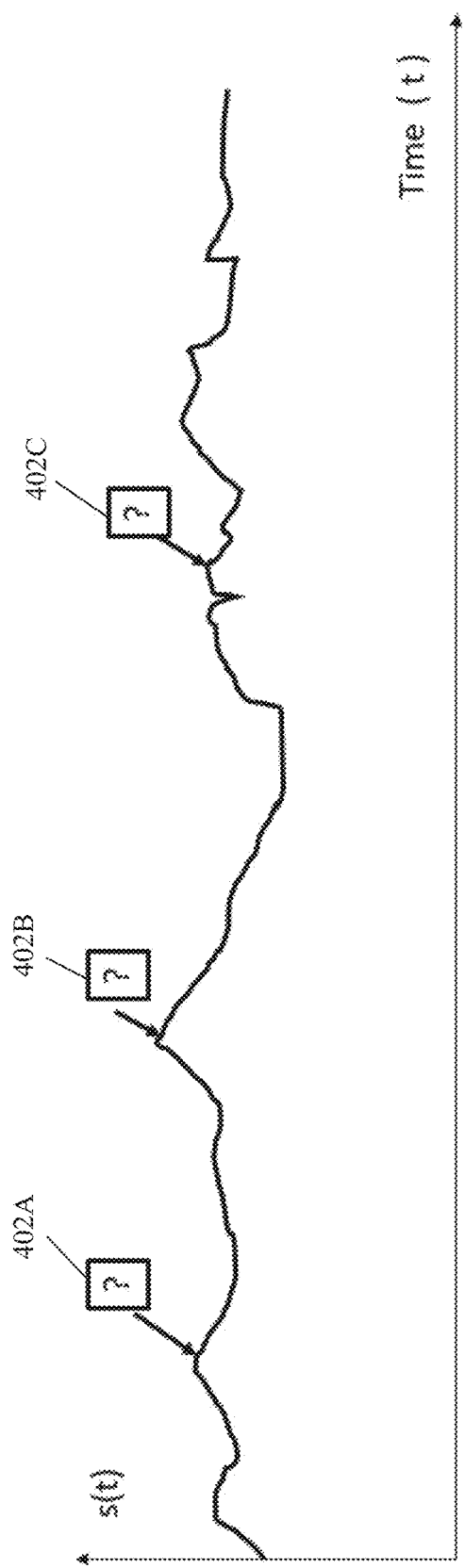
FIG. 4 is a schematic of an example of a raw signal output of a sensor placed at the LES and/or in proximity to the LES, in accordance with some embodiments of the present invention.

Reference is now made to FIG. 4, which is a schematic of an example of a raw signal output of a sensor placed at the LES and/or in proximity to the LES, for example, an impedance sensor and/or a pressure sensor, over an interval of time, in accordance with some embodiments of the present invention. The frequency of the motion of the diaphragm is not easily discernible from the time domain signal. For example, it is unclear whether any of the points 402A-C represent meaningful values, noise, or other irrelevant features.

Referring now back to FIG. 1A, at 106, an indication of the frequency of movement of the diaphragm is computed according to an analysis of the values sensed by the sensor(s) 202 located on the feeding tube, in contact with the tissue of the esophagus, at the LES and/or in proximity to the LES.

It is noted that neural signals are filtered out, since the neural signals form a common mode to the electrode pair. Alternatively or additionally, a filter may be designed to filter out neural signals, optionally neural signals associated with the diaphragm (e.g., Electromyography (EMG)), Electrocardiography (ECG) signals, and/or other neural signals senses at the LES and/or in proximity of the LES. The filter designed to filter out neural signals may be implemented, for example, as a cascade filter to the other filter(s) described herein (e.g., bandpass filter, band reject filter), and/or the other filter(s) described herein may be designed to also filter out neural signals.

Reference is now made to FIG. 1B, which is a flowchart of an exemplary method for analyzing values sensed at the LES and/or in proximity to the LES by one or more sensors, in accordance with some embodiments of the present invention. The analysis is based on a transformation of the time domain signal outputted by the sensor(s) into the frequency domain to identify peaks within selected regions of the frequency domain.

At 150, a Fourier transform of the values sensed by sensor(s) over the time interval is computed. The Fourier transform is designed to extract the frequency band of the movement of the diaphragm that is "buried" in the pressure and/or impedance signal.

In terms of mathematical representation, the Fourier transform of the raw time domain signal may be denoted as:

$$S[f(i)] = FFT\ `\{s[k]\}$$

Optionally, a maximum amplitude of the Fourier transform is identified. The frequency of the diaphragm movement is computed according to the frequency of the Fourier transform corresponding to the maximum amplitude.

The maximum amplitude of the Fourier transform may be indicative of the frequency of the movement of the diaphragm, and/or may be used to create a filter for improving the accuracy of identifying the frequency of the movement of the diaphragm.

The maximum amplitude may be identified for a local range of the Fourier transform. The local range is selected according to the most likely range of frequency of the diaphragm movement. For example, the local range is selected as about 0.2 to 0.5 Hertz (Hz). Identification of the maximum amplitude within the selected range helps exclude other local peaks related to other physiological phenomena, for example, of cardiac and/or neural origin.

A band width associated with the maximum amplitude of the Fourier transform may be identified. The band width may be denoted as the frequency range at which the amplitude of the Fourier transform is at least half the maximum amplitude. An exemplary band width is about 0.1 Hz, 0.2 Hz, or 0.3 Hz.

In terms of mathematical representation, the maximum amplitude of the Fourier transform and the band width may be respectively denoted as:

$$f\text{max and }\Delta f\text{max}$$

Figure 5:
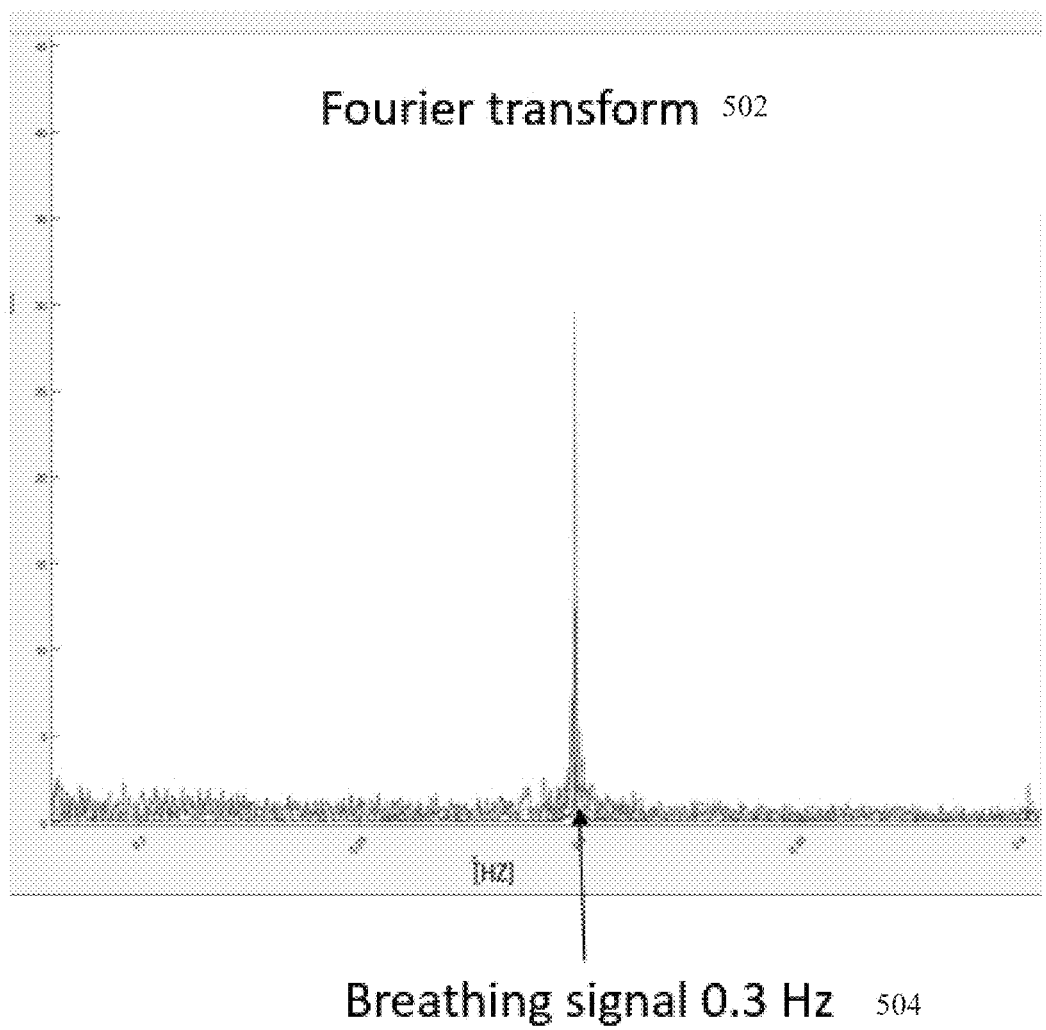
FIG. 5 is a schematic depicting a Fourier transform of a time domain signal of values measured by a sensor located within the esophagus at the LES and/or in proximity to the LES, in accordance with some embodiments of the present invention.

Reference is now made to FIG. 5, which is a schematic depicting a Fourier transform 502 of a time domain signal of values measured by a sensor located within the esophagus at the LES and/or in proximity to the LES, in accordance with some embodiments of the present invention. The maximum amplitude 504 of the Fourier transform 502 represents the frequency of the movement of the diaphragm, identified as 0.3 Hz.

Referring now back to FIG. 1B, at 152, a band pass filter may be computed based on the values measured by the sensor(s) over the time interval. The time interval may be a historical time interval for computing a band pass filter for applying to values of a current time interval, or a current time interval for computing a band pass filter for applying to values of a future time interval.

The band pass filter is computed according to a frequency corresponding to a maximum value computed from a Fourier transform of the pressure changes obtained during a historical time interval and/or according to the band width computed according to the maximum value (e.g., corresponding to the frequency range in which the values of the Fourier transform are at least half the maximum value), and according to a frequency bandwidth based on the maximum value, and applying the filter to the current signal indicative of pressure changes for computing the frequency of diaphragm movement.

The band pass filer may be implemented as a cascade of a low pass filter followed by a high pass filter.

Alternatively or additionally, a band reject filter is computed according to a spectrum band of the ventilator 230 that mechanically ventilates the target individual.

At 154, the band pass filter and/or band rejected filter is applied to the Fourier transform of the values of the current time interval (and/or a future time interval) measured by the sensor(s).

The band pass filter and/or band rejected filter may be tunable filters that are dynamically adjusted according to dynamically computed Fourier transforms of values sensed by the sensor(s) over multiple time intervals.

The band pass filter may remove signals originating from other sources which may interfere with the accuracy of obtaining the indication of frequency of movement of the diaphragm, for example, from neural based sources, cardiac based sources, instrument based sources, and/or may avoid unaccounted for delays that may exist in systems measuring neural signals.

The band pass filter may be implemented as a tunable selective filter, where the tuning instructions are obtained according to an analysis of the Fourier transform of the values measured by the sensor(s).

The band pass filer may be implemented as an analogue and/or digital filter.

Figure 6:
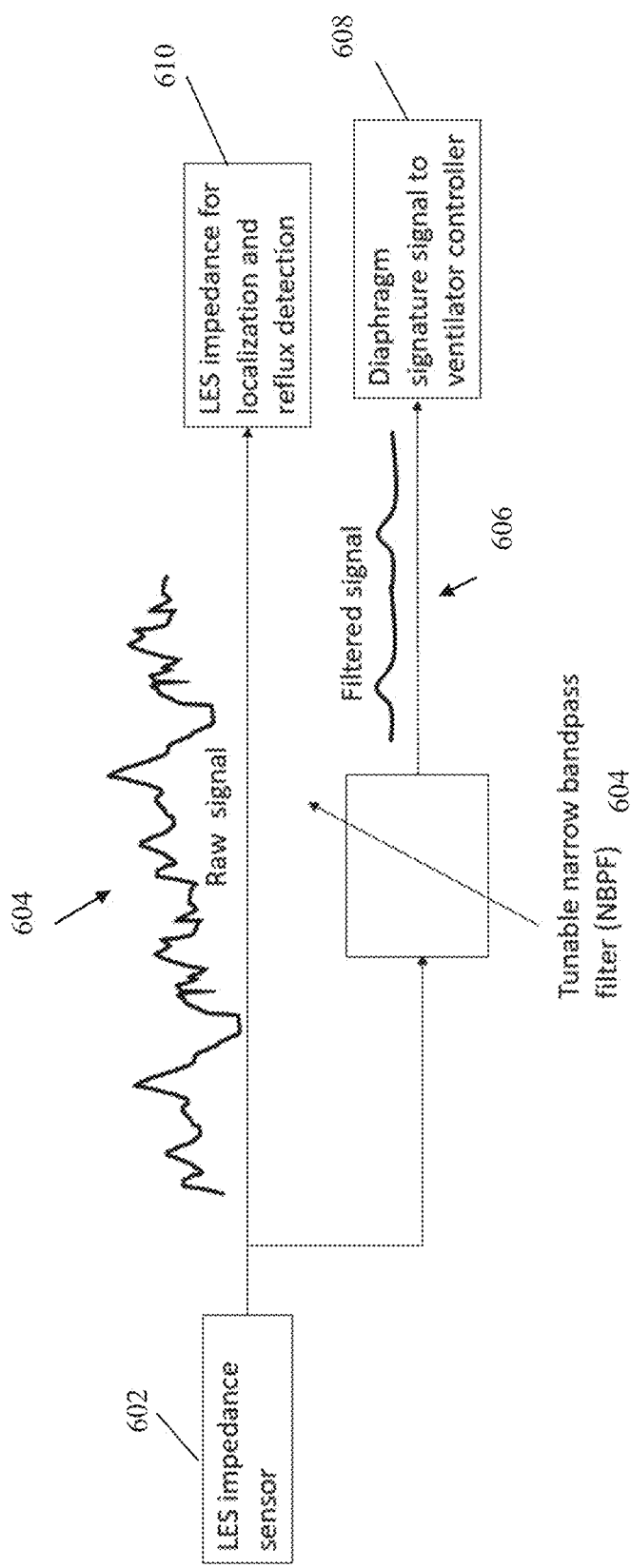
FIG. 6 is a schematic depicting processing of the output of an impedance sensor by applying the matched band pass filter, in accordance with some embodiments of the present invention.

Reference is now made to FIG. 6, which is a schematic depicting processing of output of an impedance sensor implementation of sensor 202 of FIG. 2, by applying the band pass filter, in accordance with some embodiments of the present invention. An LES impedance sensor 602 (e.g., electrode) outputs a raw time domain impedance signal 604. It is noted that the LES impedance sensor 602 is described as an example, but may be substituted by other implementations of sensor(s) 202 of FIG. 2. The raw time domain impedance signal 602 is filtered by applying a tunable narrow band pass filter (NBPF) 604 to create a filtered signal 606. The filtered signal 606 is analyzed 608 to compute the frequency of diaphragm motion, which is used to synchronize the ventilator for weaning the patient. Alternatively or additionally, the raw time domain impedance signal 604 is analyzed 610 for other applications, for example, for localization of the feeding tube, and/or detection of reflux, as described herein.

Figure 7:
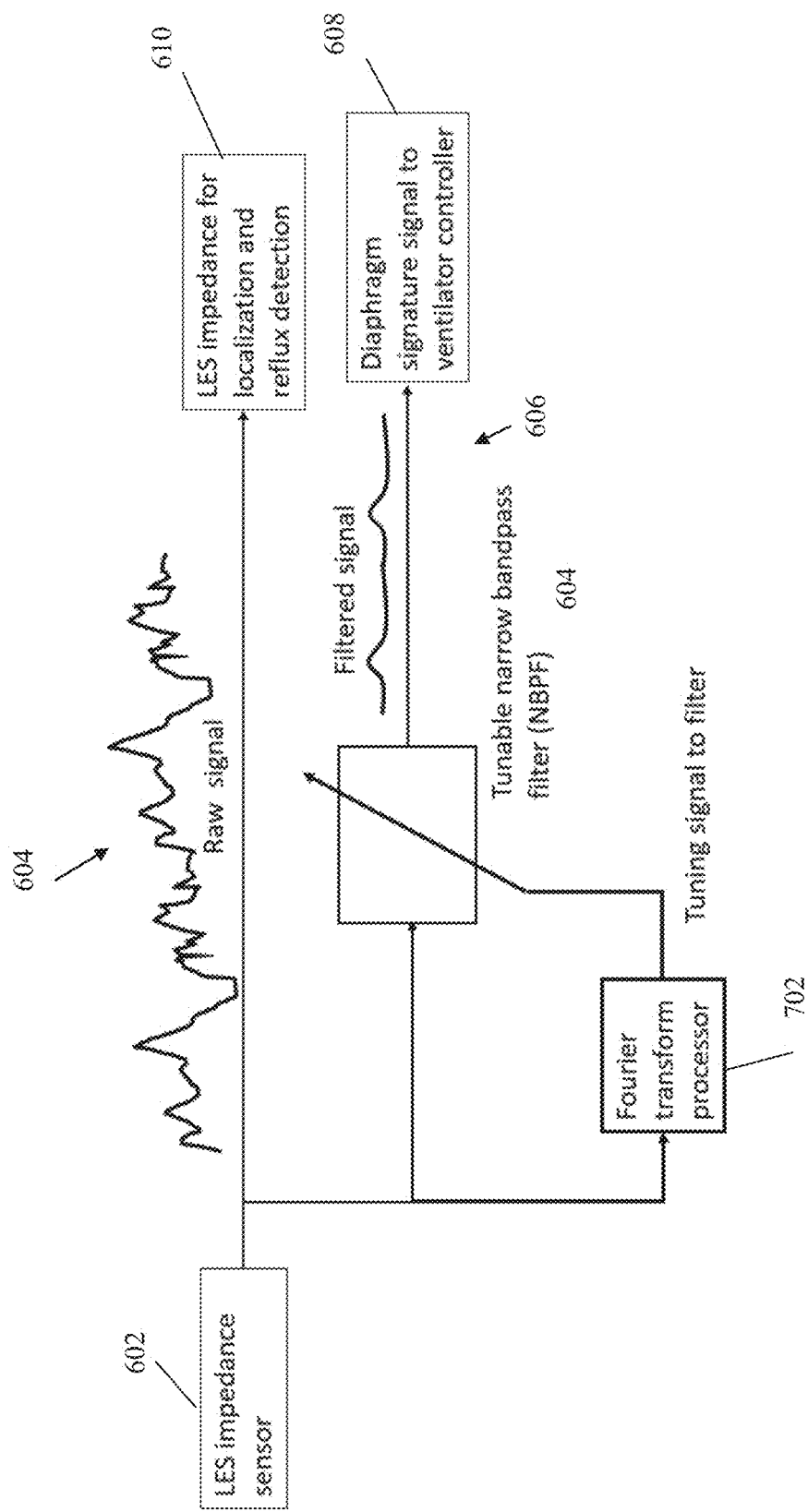
FIG. 7 is a schematic depicting processing of the current output of the impedance sensor by applying the tunable narrow band pass filter as described with reference to FIG. 6, where the band pass filter is tuned according to an analysis of a Fourier transform of historical output of the impedance sensor, in accordance with some embodiments of the present invention.

Reference is now made to FIG. 7, which is a schematic depicting processing of the current output of the impedance sensor 602 by applying the tunable narrow band pass filter 604 as described with reference to FIG. 6, where the band pass filter 604 is tuned according to an analysis of a Fourier transform 702 of historical output of the impedance sensor 602, in accordance with some embodiments of the present invention. Alternatively or additionally, the band pass filter 604 applied to the current raw output signal 604 of the impedance sensor is tuned based on an analysis of the Fourier transform of the raw signal 604 output of the impedance sensor 602. The Fourier transform 702 of the current and/or historical output signals of the impedance sensor 602 is computed, and the maximum amplitude and/or bandwidth of the Fourier transform is computed, as described herein. The NBPF 604 is tuned according to the maximum amplitude and/or bandwidth, as described herein.

Figure 8:
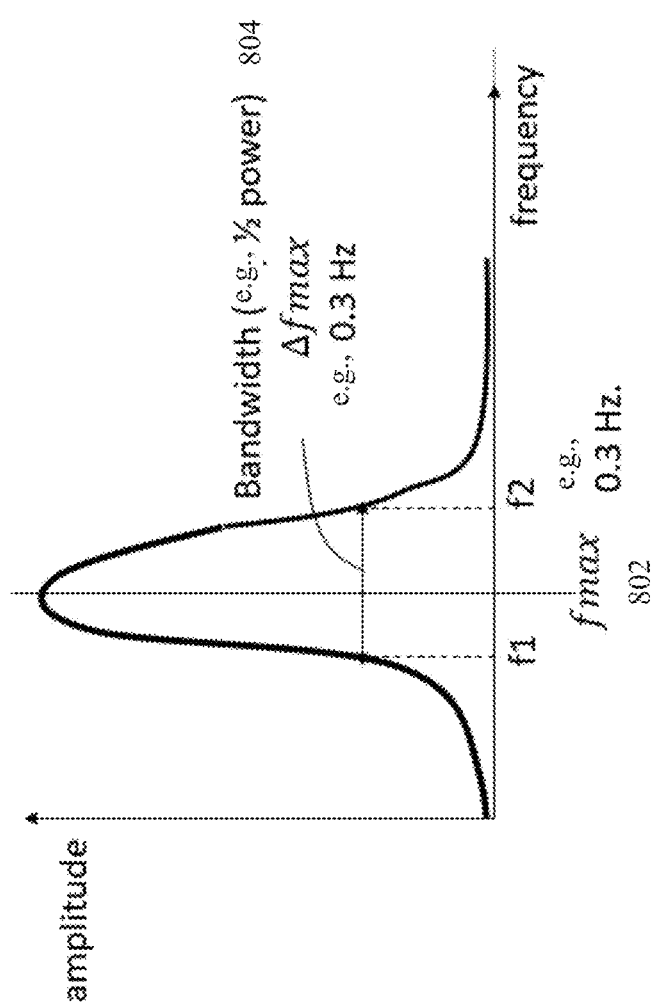
FIG. 8 is a schematic depicting a band pass filter created based on an analysis of a Fourier transform of values sensed by sensor(s), in accordance with some embodiments of the present invention.

Reference is now made to FIG. 8, which is a schematic depicting a band pass filter created based on an analysis of a Fourier transform of time domain values sensed by sensor(s) 202 of FIG. 2, in accordance with some embodiments of the present invention. The center peak value of the band pass filter is set according to the maximum amplitude of the Fourier transform of the sensor measured values, denoted fmax 802. The bandwidth 804 of the band pass filter is set according to the band width of frequencies of the Fourier transform that have an amplitude of at least half the maximum amplitude, denoted Δfmax. The bandwidth may be represented with f1 as the lower frequency of the band width range and f2 as the upper frequency of the band width range.

Figure 9:
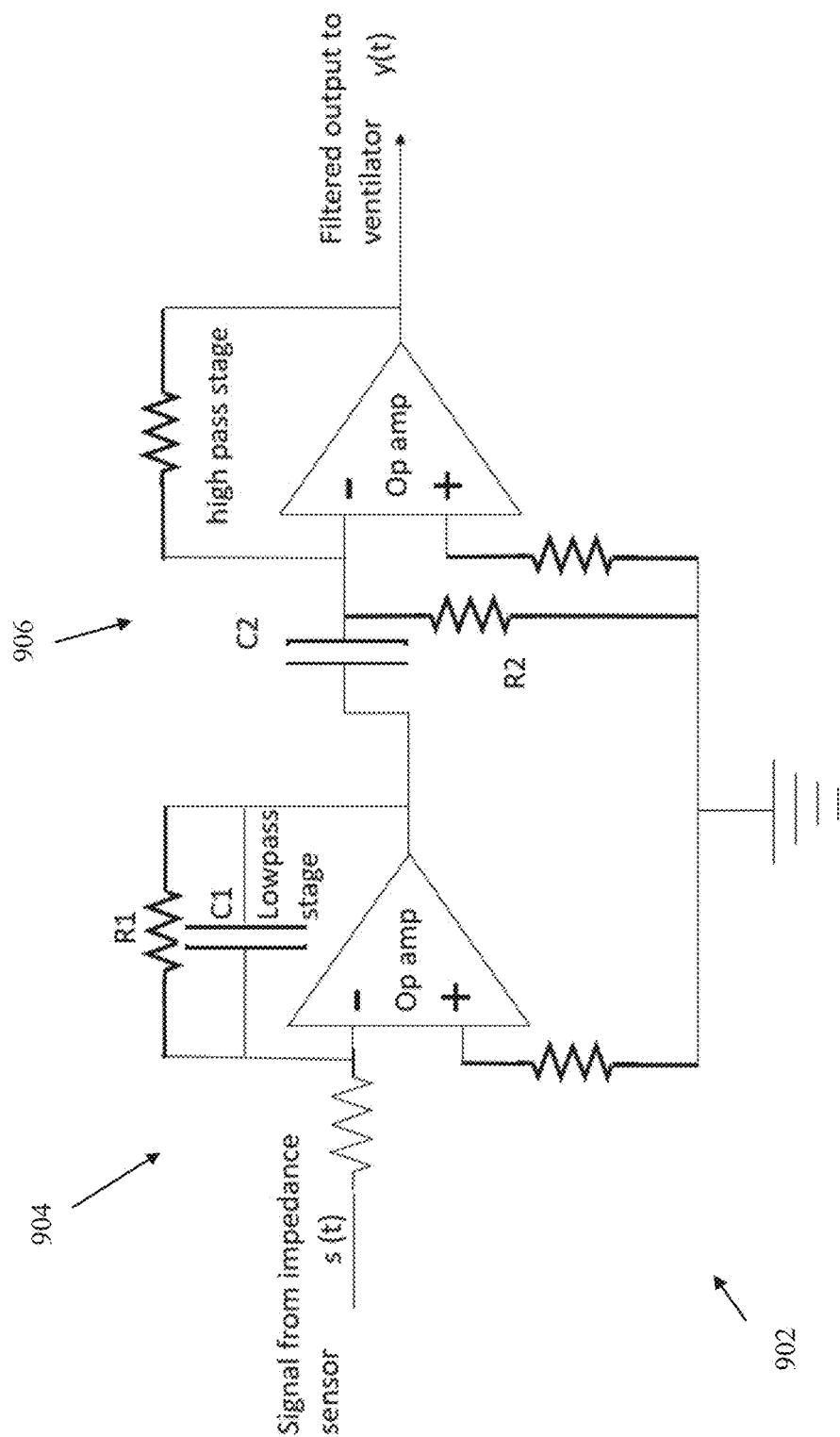
FIG. 9 is a schematic of an exemplary architecture of an analogue implementation of a band pass filter for filtering time domain values outputted by a sensor, in accordance with some embodiments of the present invention.

Reference is now made to FIG. 9, which is a schematic of an exemplary architecture of an analogue implementation of a band pass filter 902 for filtering time domain impedance values outputted by sensor(s) 202 of FIG. 2, in accordance with some embodiments of the present invention. Band pass filter 902 is implemented as a cascade of a low pass filter 904 component that filters out frequencies above a threshold, optionally f2, followed by a high pass filter 906 component that filters out frequencies below a threshold, optionally f1. The respective time constants $R_1C_1$ and $R_2C_2$ may be calculated according to the maximum frequency and band width computed according to the Fourier transform, for example, according to the following equations:

$$R_1C_1 = \frac{1}{2\pi(f\max + \Delta f\max)}$$

$$R_2C_2 = \frac{1}{2\pi(f\max - \Delta f\max)}$$

Figure 10:
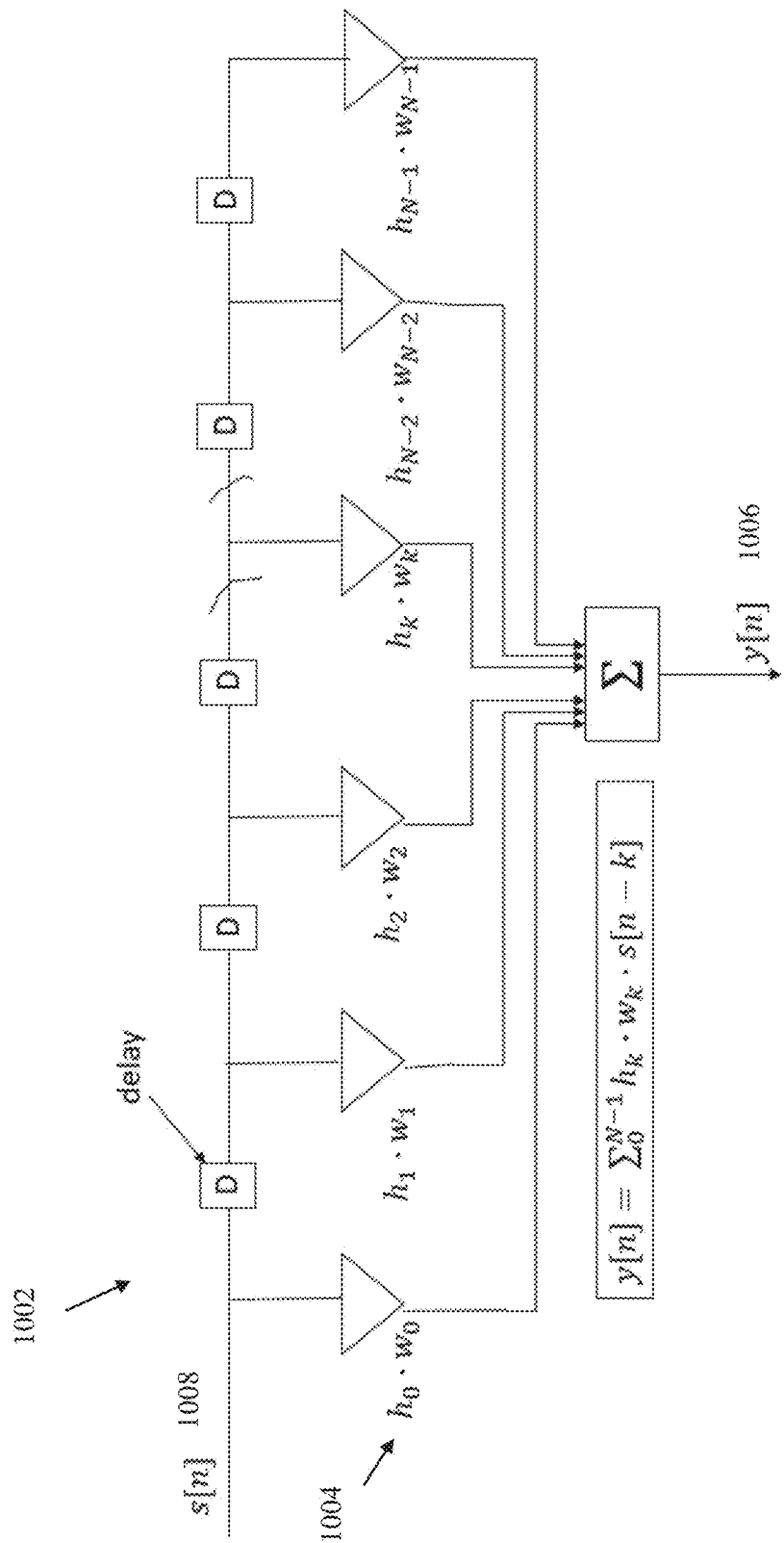
FIG. 10 is a schematic of an exemplary architecture of a digital implementation of a band pass filter for filtering time domain values outputted by a sensor, in accordance with some embodiments of the present invention.

Reference is now made to FIG. 10, which is a schematic of an exemplary architecture of a digital implementation of a band pass filter 1002 for filtering time domain values outputted by sensor(s) of FIG. 2, in accordance with some embodiments of the present invention. Band pass filter 1002 may be implemented as a finite impulse response (FIR) filter. The number of samples (i.e., values) for computation is denoted as N.

The frequencies f1 and f2 defining the band pass may be computed according to the maximum frequency and band width computed according to the Fourier transform, for example, according to the following equations: f1=fmax−Δfmax/2 and f2=fmax+Δfmax/2.

Filter coefficients $h_k$ are tuned by the band upper and lower frequencies f1, f2. h[0] to h[N−1] characterize the filter.

Filter coefficients wk are tuned according to the filter type. Window elements w[0] to w[N−1] are equal to 1 for the simple rectangular window and may poses other values when a more complex window is desired, for example, Bartlett's, Hamming's, or other windows.

Arrow 1004 denotes $h_0 * w_0$ as an example.

The operation of the FIR filter 1002 may be mathematically represented by the following equation:

$$y[n] = \Sigma_{k=0}^{k=N-1} h[k] \cdot s[n-k]$$

Where:

y[n] 1006 denotes the current digital signal output of the filtered signal.

s[n] 1008 denotes the digital input signal obtained from the sensor(s) 202 of FIG. 2.

s[k] denotes the $k^{th}$ element of the signal input vector (the last N samples, 0 to N−1) from the sensor(s) 202 of FIG. 2, a typical moving window digital window that, in the general case uses the N last sensor outputs.

h[k] denotes the $k^{th}$ element of the finite impulse response of the filter, where k=0 to k=N−1. The impulse response of a band pass filter may be computed according to the mathematical relationships:

$$h[k] = \frac{\sin(k-n)\omega_2}{\pi(k-n)} - \frac{\sin(k-n)\omega_1}{\pi(k-n)} \forall k < N - 1$$

$$h(N-1) = \frac{\omega_2 - \omega_1}{\pi}$$

$$\omega_1 = \frac{2\pi\left(f\max - \frac{\Delta f\max}{2}\right)}{f\text{sampling}}$$

$$\omega_2 = \frac{2\pi\left(f\max + \frac{\Delta f\max}{2}\right)}{f\text{sampling}}$$

where fmax and Δfmax are computed from the Fourier transform as described herein.

Referring now back to FIG. 1A, at 106, the indication of frequency of diaphragm movement is computed according to the Fourier transfer of the values sensed by sensor(s) 202, optionally of the filtered Fourier transform.

Compensation of the filtered Fourier transform for significant phase delay may be performed.

At 108, instructions for adjustment of one or more parameters of ventilator 230 are generated according to the computed frequency of diaphragm movement. The instructions may include instructions for adjustment of the ventilation frequency, by synchronizing administration of ventilation cycles according to the computed frequency of diaphragm movement.

The natural diaphragm rhythm may be used to trigger the ventilator in synchronization with the natural diaphragm motion. The synchronization may speed up the process of weaning the patient, and/or to restore normal spontaneous breathing, which is the rationale behind at least some of the systems, apparatus, methods, and/or code instructions described herein.

The instructions may be transmitted to ventilator 230 from computing device 206 over network 226 for automatic adjustment of ventilator 230 (via a phase-locked loop (PLL) loop and/or a correlation tracking loop). The instructions may be presented on a display, for review by a user (e.g., attending physician, ventilation machine technician). The user may review the instructions and authorize the automatic adjustment of the parameters. Alternatively or additionally, the instructions may be for manual adjustment of ventilator 230 by a user. The manual instructions may be presented on a display of computing device 206 and/or transmitted to client terminal 222 and/or server 224 for presentation on a display.

At 110, acts of blocks 104-108 are iterated over multiple time intervals. The iterations monitor the frequency of diaphragm movements of the ventilated target individual, and may dynamically adjust the parameters of the ventilator for weaning the target individual according to dynamic changes of the frequency of diaphragm movements. Reference is now made to FIG. 1C, which is the flowchart of the method of FIG. 1A including some additional optional features, in accordance with some embodiments of the present invention. Blocks 102-110 are as described with reference to FIG. 1A.

At 112, a trend curve may be computed according to multiple diaphragm movement frequencies measured over multiple historic time intervals. The trend curve may be computed, for example, as a linear regression according to the multiple diaphragm movement frequencies.

Optionally, a future frequency of diaphragm movement at a future time interval is predicted according to the trend curve.

At 114, an alert may be generated. The alert may be triggered when the diaphragm movement frequency is according to a requirement, for example, above a threshold, below a threshold, within a range, or outside of a range. The alert may indicate that the target individual is attempting self breathing and/or is otherwise ready for weaning.

The alert may be triggered when the predicted diaphragm movement frequency is according to a requirement, for example, above a threshold, below a threshold, within a range, or outside of a range. The alert may indicate that the target individual is predicted to attempt self breathing and/or otherwise is predicted to be ready for weaning.

The alert may be transmitted to another device, for example, of a client terminal, a mobile device, and a monitoring station server. The alert may, for example, presented on a screen, sent as an email and/or text message, and/or played as an audio message (e.g., audio file and/or phone call).

At 116, one or more additional features may be executed based on computed impedance and/or pressure measured by the sensor(s) (e.g., electrode(s)), optionally located on a balloon at the distal end of the feeding tube and/or on the tube itself at the LES area. The same electrodes and/or balloon located on the feeding tube within the esophagus may perform one or more additional features, in addition to the estimation of the frequency band of movement of the diaphragm:

Exemplary additional features include one or more of:

* Estimating an amount of lung fluid in the patient. When inflated, electrode(s) located on the surface of the balloon contacts the inner wall of the esophagus to measure electrical parameters (e.g., impedance) for estimating an amount of lung fluid in the patient. Additional details of an exemplary implementation of feeding tube 212 and balloon that is inflated to sense lung fluid may be found with reference to International Patent Application No. IB2017/057702, to the same inventors and the same assignee, the contents of which are incorporated herein by reference in their entirety.

* Monitoring a position of the tube within the digestive system based on an analysis of the applied alternating current and measured voltage drop. For example, to detect when the tube moves out of the correct position. Impedance values sensed by the impedance sensor(s) are analyzed for monitoring the position of the feeding tube 212 within the esophagus, for example, as described with reference to U.S. Pat. No. 9,713,579, by the same inventors of the present application, to the same inventors and the same assignee, the contents of which are incorporated herein by reference in their entirety.

* Estimating a level of fluid within the digestive system based on an analysis of the applied alternating current and measured voltage drop. The enteral feeding rate delivered by the feeding tube may be automatically adjusted according to the estimated fluid level, for example, to prevent reflux. Additional details of exemplary systems and/or methods for estimating fluid levels based on impedance measurements computed based on impedance sensor(s) located on a feeding tube positioned within the esophagus may be found with reference to International Patent Application No. IL2015/051156, by the same inventors of the present application.

* Detecting a gastric reflux event based on an analysis of the applied alternating current and measured voltage drop. For example, to stop enteral feeding. Optionally, when a gastric reflux event is detected, the estimation of lung fluid may be stopped and/or adjusted to account for the gastric reflux event, for example, by subtracting the computed impedance value (denoting total impedance due to lung fluid and reflux) from the estimated impedance value due to the presence of fluid in the esophagus due to the reflux. When no gastric reflux event is detected, the measured impedance may be assumed to be an indication of lung fluid without interference effects due to the presence of fluid within the esophagus (i.e., the reflux). Additional details of exemplary systems and/or methods for detecting reflux event based on impedance measurements computed based on electrode(s) located on a tube positioned within the esophagus may be found with reference to International Patent Application No. IL2017/050634, by the same inventors of the present application.

At 118, acts of blocks 104-116 are iterated over multiple time intervals. The iterations monitor the frequency of diaphragm movements of the ventilated target individual, and may dynamically adjust the settings of the ventilator for weaning the target individual according to dynamic changes of the frequency of diaphragm movements. Additional features may be executed during one or more of the iterations.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant sensors and feeding tubes will be developed and the scope of the terms sensor and feeding tube are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for mechanically ventilating a target individual, the system comprising:
   a feeding tube for insertion into a distal end of an esophagus of the mechanically ventilated target individual;
   at least one sensor comprising at least one electrode for sensing impedance values disposed near a distal end of the feeding tube at a location such that the at least one electrode is located at the distal end of the esophagus of the target individual when the feeding tube is located within the esophagus and in use, wherein the at least one electrode is positioned for sensing impedance values when contacting tissue of the esophagus including at least one of a lower esophageal sphincter (LES) and tissue in proximity to the LES;
   and
   a non-transitory memory having stored thereon a code that in response to execution by at least one hardware processor of a computing device, causes the computing device to extract a frequency band of diaphragm movement and a phase of the diaphragm movement of the mechanically ventilated target individual from the impedance values sensed by the at least one electrode that include much larger amplitude signals generated based on a mechanical ventilator, and compute instructions to adjust ventilation frequencies and ventilation phases of the mechanical ventilator for mechanically ventilating the target individual by synchronizing to a waveform of the diaphragm movement in frequency band and phase of diaphragm movement for matching a waveform of the ventilator to the waveform of the diaphragm movement;
   wherein the instructions to adjust the ventilation frequencies and the ventilation phases of the waveform of the mechanical ventilator are computed while the feeding tube is in use for feeding the individual and while the at least one electrode senses impedance values by contacting the tissue of the esophagus including at least one of the LES and tissue in proximity to the LES.

2. The system according to claim 1, wherein the at least one electrode is mounted on an inflatable balloon located at the distal end of the feeding tube, wherein when the inflatable balloon is inflated the at least one electrode contacts the tissue of the esophagus.

3. The system according to claim 1, further comprising:
   at least one esophageal body having a pressure dependent volume, coupled to a distal portion of the feeding tube, wherein the at least one esophageal body is adapted to contact the tissue of the esophagus when inflated; and
   wherein the at least one sensor comprises a pressure sensor that senses the pressure in the at least one esophageal body when inflated.

4. The system according to claim 1, wherein the at least one sensor adapted to contact at least one of the LES and tissue in proximity to the LES comprises a pressure sensor that senses pressure changes created by the movement of the diaphragm.

5. The system according to claim 1, further comprising code that in response to execution by at least one hardware processor of the computing device, causes the computing device to compute a Fourier transform of a current signal indicative of current values sensed by the at least one sensor, identify a maximum value of the Fourier transform, and compute the frequency band of diaphragm movement according to a frequency and amplitude corresponding to the maximum value.

6. The system according to claim 5, wherein the maximum value of the Fourier transform is identified within the range of about 0.2 to 0.5 hertz (Hz).

7. The system according to claim 5, further comprising code that in response to execution by at least one hardware processor of the computing device, causes the computing device to compute a band pass filter based on values sensed by the at least one sensor during a historical time interval, the band pass filter computed according to a frequency and phase corresponding to a maximum value computed from a Fourier transform of pressure values obtained during a historical time interval, and according to a frequency bandwidth based on the maximum value, and apply the filter to the current signal indicative of pressure values to compute the frequency band and phase of diaphragm movement.

8. The system according to claim 7, wherein the frequency bandwidth is computed according to a frequency range in which values of the Fourier transform are at least half of the maximum value.

9. The system according to claim 7, wherein the band pass filter comprises a cascade of a low pass filter followed by a high pass filter.

10. The system according to claim 1, further comprising code that in response to execution by at least one hardware processor of the computing device, causes the computing device to compute a band reject filter according to a spectrum band of the mechanical ventilator, and removing interference signals of the mechanical ventilator from the values sensed by the at least one sensor by applying the band reject filter to the values sensed by the at least one sensor.

11. The system according to claim 1, wherein the at least one sensor is located within about 0-5 centimeters from the lower esophageal sphincter when contacting the tissue of the esophagus, when the system is in use.

12. The system according to claim 1, further comprising:
code that in response to execution by at least one hardware processor of the computing device, causes the computing device to compute a trend curve according to a plurality of diaphragm movement frequencies measured over a plurality of time intervals; and
predict a future frequency of diaphragm movement at a future time interval according to the trend curve.

13. The system according to claim 12, further comprising:
code that in response to execution by at least one hardware processor of the computing device, causes the computing device to generate an alert for presentation on a display of a client terminal when the future frequency of diaphragm movement at the future time interval is predicted to meet a requirement.

14. The system according to claim 1, wherein the mechanical ventilator is a conventional mechanical ventilator that ventilates the target individual at a frequency within a normal respiratory rate.

15. The system according to claim 1, further comprising code for computing a filter for filtering of neural signals, and for applying the filter to values sensed by the at least one sensor.

16. A method for mechanically ventilating a target individual, the method comprising:
providing a feeding tube for insertion into a distal end of an esophagus of the mechanically ventilated target individual, the feeding tube including at least one sensor comprising at least one electrode for sensing impedance values disposed near a distal portion thereof;
sensing impedance values by the at least one sensor, when the at least one electrode is located at the distal end of the esophagus of the target individual when the feeding tube is located within the esophagus and in use, wherein the at least one electrode senses impedance values when contacting tissue of the esophagus including at least one of a lower esophageal sphincter (LES) and tissue in proximity to the LES;
extracting a frequency band of diaphragm movement and phase of diaphragm movement of the mechanically ventilated target individual from the impedance values sensed by the at least one electrode that include much larger amplitude signals generated based on a mechanical ventilator; and
computing instructions to adjust ventilation frequencies and ventilation phases of the mechanical ventilator for mechanically ventilating the target individual by synchronizing to a waveform of the diaphragm movement in frequency band and phase of diaphragm movement for matching a waveform of the ventilator to the waveform of the diaphragm movement;
wherein the instructions to adjust the ventilation frequencies and the ventilation phases of the waveform of the mechanical ventilator are computed while the feeding tube is in use for feeding the individual and while the at least one electrode senses impedance values by contacting the tissue of the esophagus including at least one of the LES and tissue in proximity to the LES.

17. The method of claim 16, wherein the frequency band of diaphragm movement of the mechanically ventilated target individual is within the range having a lower cutoff of greater than 0.2 Hz and a higher cutoff of about 0.5 Hz.

18. The method of claim 16, wherein the frequency band of diaphragm movement of the mechanically ventilated target individual is within the range having a lower cutoff of over 12 breathes per minute and a higher cutoff of about 40 breathes per minute.

19. The method of claim 16, further comprising creating a phase locked loop between the extracted frequency band and phase of diaphragm movement and the mechanical ventilator.

20. The method of claim 16, wherein the frequency band and phase of the diaphragm movement of the mechanically ventilated target individual are different than motion of the lungs of the target individual corresponding to a frequency setting of the mechanical ventilator that forces air in and out of the target individual.

21. The method of claim 16, wherein the frequency band and phase of the diaphragm are extracted using a Fourier transform of the impedance values, and by applying a bandpass reject filter designed to exclude the signals associated with the mechanical ventilator and include signals associated with movement of the diaphragm.

* * * * *